(12) United States Patent  
Farrell

(10) Patent No.: US 8,627,601 B2  
(45) Date of Patent: Jan. 14, 2014

(54) ROTATING RADIATION SHIELDED ENTRANCE ASSEMBLY

(75) Inventor: David P. Farrell, Malvern, PA (US)

(73) Assignee: Veritas Medical Solutions LLC, Malvern, PA (US)

( * ) Notice: Subject to any disclaimer, the term of this patent is extended or adjusted under 35 U.S.C. 154(b) by 0 days.

(21) Appl. No.: 13/332,958

(22) Filed: Dec. 21, 2011

(65) Prior Publication Data

US 2012/0159849 A1 Jun. 28, 2012

Related U.S. Application Data

(60) Provisional application No. 61/426,609, filed on Dec. 23, 2010.

(51) Int. Cl.  
*E06B 3/34* (2006.01)

(52) U.S. Cl.  
USPC .................................. 49/41; 49/40

(58) Field of Classification Search  
USPC ............ 49/40, 41, 42, 49, 26, 28; 109/48, 61, 109/59 T, 64  
See application file for complete search history.

(56) References Cited

U.S. PATENT DOCUMENTS

| | | | | |
|---|---|---|---|---|
| 841,696 | A * | 1/1907 | Lang .................................. | 49/68 |
| 3,085,464 | A * | 4/1963 | Touvay ............................ | 49/41 |
| 3,658,277 | A * | 4/1972 | Anderson ...................... | 244/1 R |
| 4,385,469 | A * | 5/1983 | Scheuerpflug et al. ........... | 49/41 |
| 4,557,073 | A * | 12/1985 | Sandling ........................... | 49/41 |
| 4,843,761 | A * | 7/1989 | Sandling ........................... | 49/41 |
| 4,932,553 | A | 6/1990 | Reich, Jr. et al. | |
| 5,605,014 | A * | 2/1997 | Kimura .............................. | 49/40 |
| 5,770,934 | A * | 6/1998 | Theile ........................... | 318/469 |
| 5,851,182 | A | 12/1998 | Sahadevan | |
| 5,963,000 | A * | 10/1999 | Tsutsumi et al. ............. | 318/480 |
| 6,266,922 | B1 * | 7/2001 | Rockenbach ..................... | 49/42 |
| RE37,467 | E | 12/2001 | Brasch et al. | |
| 7,104,008 | B2 * | 9/2006 | Yokotachi ......................... | 49/42 |
| 7,249,737 | B2 * | 7/2007 | Simmons et al. .......... | 244/129.5 |
| 2003/0182864 | A1 * | 10/2003 | Yokotachi ......................... | 49/40 |
| 2005/0167613 | A1 | 8/2005 | Bol et al. | |
| 2009/0110152 | A1 | 4/2009 | Manzke et al. | |
| 2009/0189560 | A1 | 7/2009 | Taheri et al. | |
| 2010/0050525 | A1 * | 3/2010 | Blasi ................................ | 49/26 |

OTHER PUBLICATIONS

International Search Report and Written Opinion issued May 1, 2012 in counterpart International Patent Application No. PCT/US11/66440.

International Preliminary Report of Patentability dated Apr. 2, 2013 in counterpart International Patent Application No. PCT/US11/66440.

* cited by examiner

*Primary Examiner* — Katherine Mitchell  
*Assistant Examiner* — Scott Denion  
(74) *Attorney, Agent, or Firm* — Volpe and Koenig, P.C.

(57) ABSTRACT

A rotating entrance assembly is provided, the rotating entrance assembly including a rotating base, a motor in driving connection with the rotating base, and first and second shielding components that are arranged on the rotating base. A passageway is defined between the first and second shielding components.

21 Claims, 5 Drawing Sheets

ROTATING RADIATION SHIELDED
ENTRANCE ASSEMBLY

CROSS REFERENCE TO RELATED APPLICATION

This application claims the benefit of U.S. Provisional Patent Application No. 61/426,609, filed Dec. 23, 2010, which is incorporated by reference as if fully set forth herein.

FIELD OF INVENTION

This application is generally related to entrances for radiation treatment rooms utilizing high energy radiation such as for particle facilities and linear accelerator rooms.

BACKGROUND

Radiation shielded facilities, especially those involving high energy X radiation or neutron radiation, require particularly thick walls and barriers. As a consequence, these rooms need a shielded passageway or a long maze to prevent radiation from escaping the shielded space. Particle accelerators use electromagnetic fields to propel charged particles, such as electrons, protons, or ions, at high speeds along defined beams. One type of particle accelerator is a linear particle accelerator, also known as a linac, which increases the velocity of charged particles by subjecting the charged particles to a series of oscillating electric potentials along a linear beam line. Linacs are commonly used to generate x-rays for medical purposes. Due to radiation from particle accelerators, particle facilities must be designed and constructed to provide adequate shielding. Known particle facilities are generally constructed as a room housing the source of radiation, with concrete walls, ceilings, and floors that can reach thicknesses of up to 15 feet. In addition, a maze entry is usually used to provide a wing wall to capture scatter radiation. The entrance to a maze entry or direct entry particle facility includes at least one shielded door to further prevent radiation leakage to the outside of the room. The shielded door for a particle facility is generally constructed as a hinged door having a very thick core, for example 20 inches thick, to provide sufficient shielding. Known shielded doors are also extremely heavy, typically 10,000-20,000 lbs for medical radiation treatment rooms, and cannot be opened and closed quickly. The time that it takes to open and close a shielded door is especially important in particle facilities where an operator may need to enter and exit the room repeatedly to make adjustments. For example, in medical applications, several rounds of low energy radiation may be used for diagnostic purposes and patient positioning before treating the patient's tumor with the high energy radiation. After each round of low energy radiation, the operator must either progress down a very long maze corridor leading to the treatment room or alternatively wait for the shielded door to fully open before entering the treatment room to make adjustments to the patient, and then wait for the shielded door to fully close again before starting the next round of low energy radiation testing or high energy radiation treatment. This process can be very time consuming and tiring to the patient. In addition, in direct entry or mini maze entry particle facilities, two shielded doors may be required to ensure sufficient shielding at the entrance. Accordingly, the two shielded doors must be synchronized to open and close at the same time, or individually opened and closed, which further increases the time it takes to access the treatment room.

A need exists for an entrance assembly that is suitable for use in particle facilities, provides adequate shielding, and allows quick access in and out of the particle facility.

SUMMARY

A rotating entrance assembly is disclosed. The rotating entrance assembly includes a rotating base, a motor in driving connection with the rotating base, and first and second shielding components that are arranged on the rotating base and define a passageway therebetween. The motor may be positioned below the rotating base and accessed through a removable panel formed in the rotating base. The rotating entrance assembly may further include a sensor arranged on at least one of the first shielding component, the second shielding component, or the rotating base, the sensor being configured to detect whether an object is in the passageway. The sensor may further be configured to relay signals to a control system electrically connected to the motor to control operation of the rotating entrance assembly.

Another rotating entrance assembly is disclosed. The rotating entrance assembly includes a frame, a motor driven rotating base positioned in the frame, and first and second shielding components supported on the rotating base to define a passageway therebetween. The first and second shielding components and the rotating base rotate together with respect to the frame.

A hinge-less entrance assembly for installation in an existing entryway is also disclosed. The hinge-less entrance assembly includes a base that rotates about a vertical axis located substantially at a center of the base, a motor that drives the base, and first and second shielding components arranged at a distance apart on opposing sides of the base. A passageway is defined between the first and second shielding components.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangement shown.

DETAILED DESCRIPTION OF THE PREFERRED EMBODIMENTS

Figure 1:
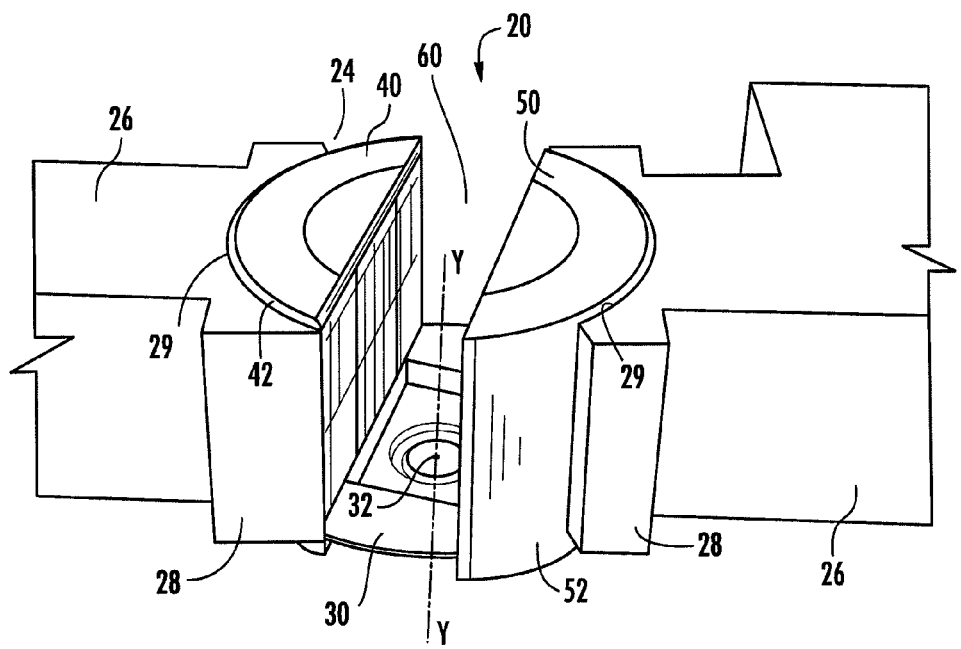
FIG. 1 is a front perspective view of an embodiment of the rotating entrance assembly.

Certain terminology is used in the following description for convenience only and is not limiting. The words "above", "below", "inner", and "outer" designate directions in the drawings to which reference is made. A reference to a list of items that are recited as "at least one of a, b, or c" (where a, b, and c represent the items being listed) means any single one of the items a, b, or c, or combinations thereof. The terminology includes the words specifically noted above, derivatives thereof, and words of similar import.

Figure 2:
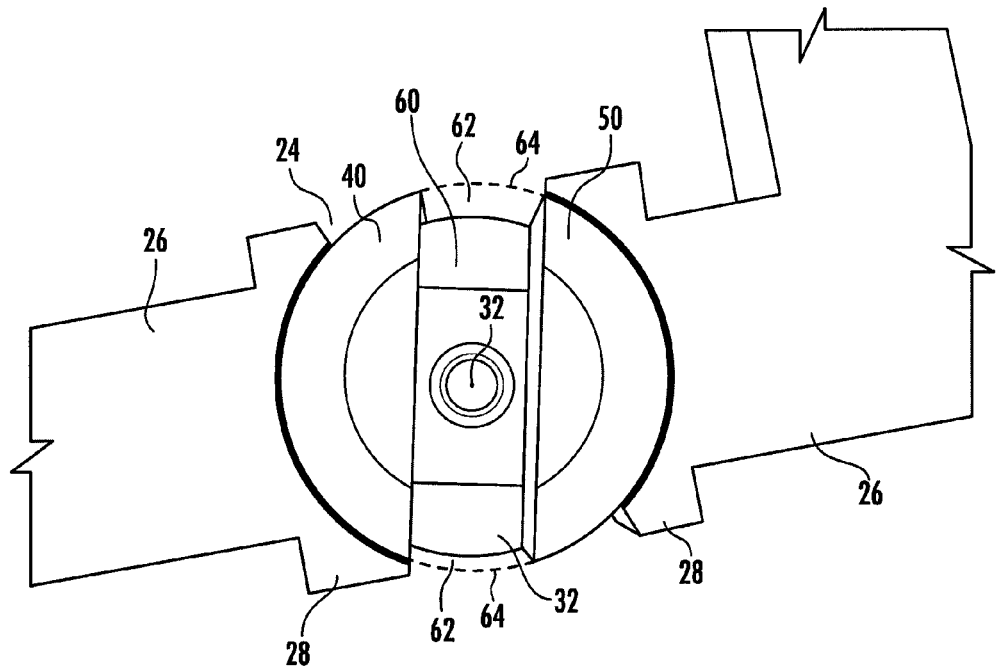
FIG. 2 is a top view of the rotating entrance assembly shown in FIG. 1.
Figure 3:
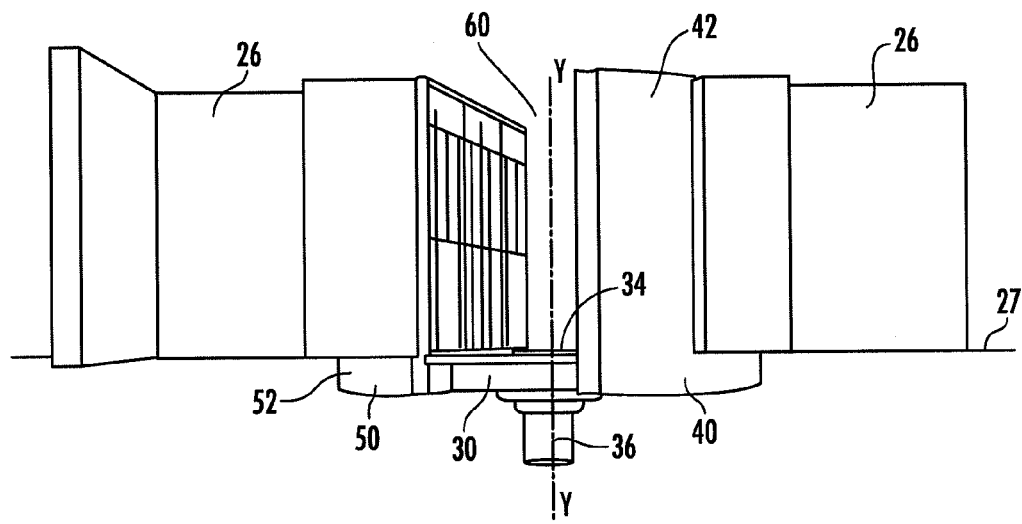
FIG. 3 is a back perspective view of the rotating entrance assembly shown in FIG. 1.

FIGS. 1-3 show an embodiment of a rotating entrance assembly 20 according to the present application. The rotating entrance assembly 20 is positioned in an existing entryway 24 formed in a wall 26, such as a shielded wall of a particle facility. The entryway 24 may include a frame 28 shaped to receive the rotating entrance assembly 20. The rotating entrance assembly 20 is positioned within the entryway 24 and includes a rotating base 30, a motor 36 in driving connection with the rotating base 30, and first and second shielding components 40, 50 that are arranged on the rotating base 30 and define a passageway 60 therebetween. While a motor 36 is generally used to drive the rotating base 30, the rotating entrance assembly 20 may also be manually operated or operated using any known rotating means. If the rotating entrance assembly 20 is used in a particle facility, the first and second shielding components 40, 50 may each be formed of a material adapted to reflect, attenuate, or capture charged particles, such as that described in U.S. patent application Ser. No. 13/060,157 and PCT Application No. PCT/US2011/036934, which are incorporated by reference as if fully set forth herein. For example, if the rotating entrance assembly 20 is used in a proton facility, the material of the first and second shielding components 40, 50 should be selected to capture neutrons. If the rotating entrance assembly 20 is used in a linac facility, the material of the first and second shielding components 40, 50 should be selected to capture x-rays and neutrons. Each one of the first and second shielding components 40, 50 may have a curved outer contour 42, 52 that corresponds with a curved inner contour 29 of the entryway 24 or frame 28. The width of the passageway 60 defined between the first and second shielding components 40, 50 may vary depending on the type of facility the rotating entrance assembly 20 is used in, but should at least be suitable for a person to walk through, for example approximately 36-46 inches wide. In research or medical particle facilities, the passageway 60 may be wider to accommodate equipment to be moved in and out of the facility, such as wheel chairs, stretchers, and lab equipment. In addition, one or both of the first and second shielding components 40, 50 can be removable in order to create additional space to move equipment in and out of the facility.

The rotating base 30 and first and second shielding components 40, 50 rotate together with respect to the entryway 24. In other words, every part of the rotating entrance assembly 20 rotate together as a unit, except for the motor 36, which may be positioned below the rotating base 30 and secured in the floor. The motor 36 can be accessed for maintenance or repair through a removable panel (shown removed in FIG. 1) formed in the rotating base 30. The first and second shielding components 40, 50 are each supported on the rotating base 30 and positioned such that the rotating base 30 is balanced. This balancing can be achieved by arranging the first and second shielding components 40, 50 at a distance apart on opposing sides of the rotating base 30, evenly spaced from a center 32 of the rotating base 30. As shown in FIGS. 1 and 3, the rotating base 30 rotates about a vertical axis Y-Y located substantially at the center 32 of the rotating base 30. The rotating base 30 can have any suitable shape. Preferably, the rotating base 30 is substantially circular and each one of the first and second shielding components 40, 50 has a substantially D-shaped cross-section, as shown in FIG. 2. Unlike traditional hinged doors, which must be mounted above the floor so that the door can open and close, portions of the rotating entrance assembly 20 according to the present application can extend beneath the floor 27, as shown by FIG. 3. Specifically, the rotating base 30 and first and second shielding components 40, 50 can extend into the floor 27 so that a top surface 34 of the rotating base 30 is even with a top surface of the floor 27.

Figure 4:
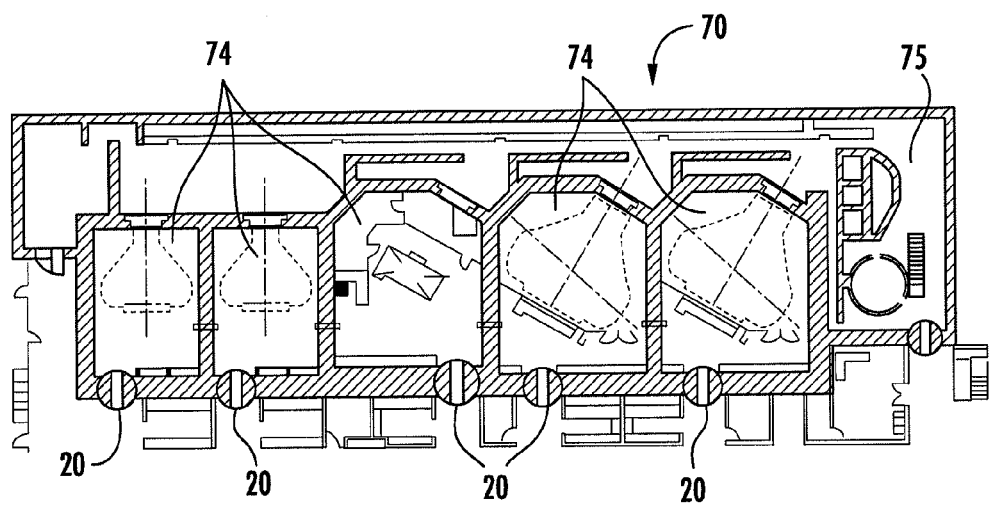
FIG. 4 is a top view of a particle facility equipped with a plurality of rotating entrance assemblies shown in FIG. 1, wherein each of the rotating entrance assemblies is in a fully open position.
Figure 5:
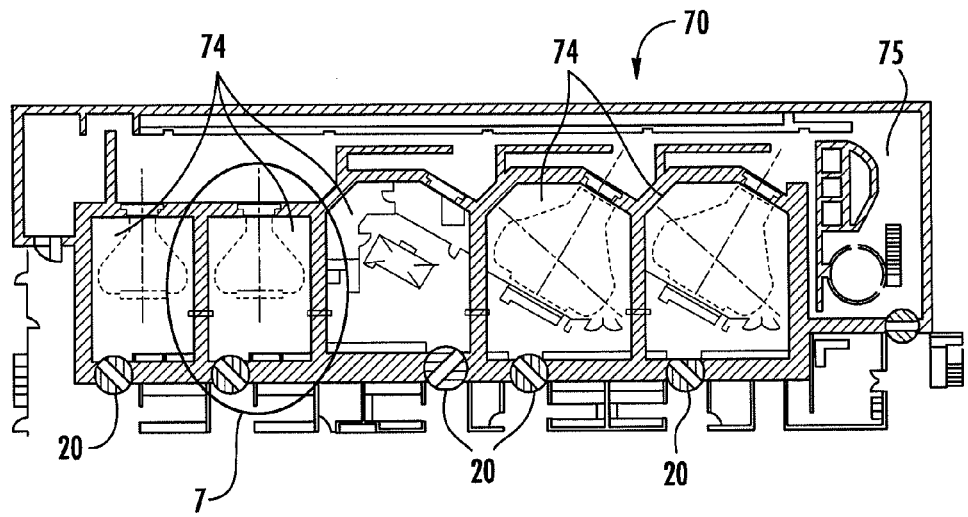
FIG. 5 is a top view of the particle facility shown in FIG. 4, wherein the treatment room rotating entrance assemblies are in a diagnostic open position.
Figure 6:
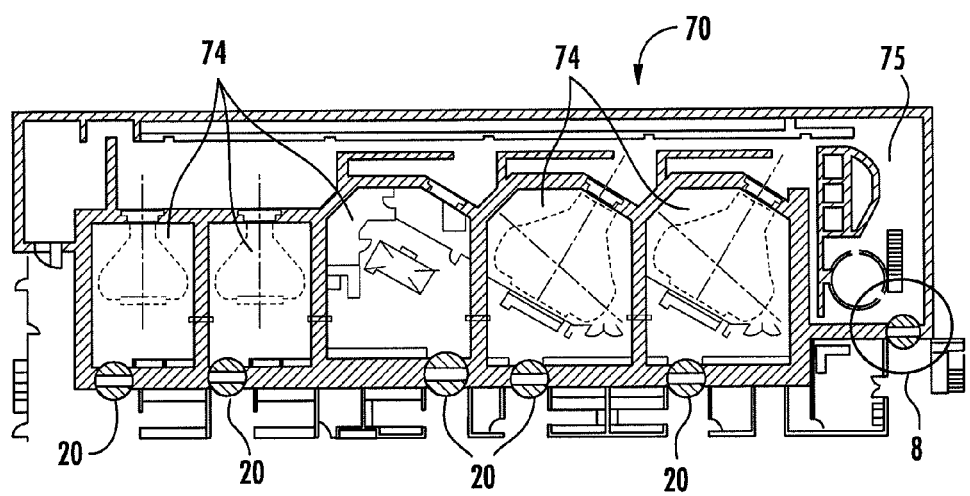
FIG. 6 is a top view of the particle facility shown in FIG. 4, wherein the rotating entrance assemblies are in a fully closed position.

In operation, the rotating base 30 and first and second shielding components 40, 50 rotate between a fully open position, in which the passageway 60 is substantially parallel to the entryway 24 or frame 28 formed in the wall 26, and a fully closed position, in which the passageway 60 is substantially perpendicular to the entryway 24 or frame 28. FIG. 4 shows a particle facility 70 having a plurality of treatment or examination rooms 74 and a particle accelerator room 75, each having a rotating entrance assembly 20 shown in the fully open position. FIG. 6 shows the same particle facility 70 with each one of the rotating entrance assemblies 20 shown in the fully closed position. When the rotating entrance assembly 20 is in the fully open position (as shown in FIG. 4) or a diagnostic open position (as shown in FIG. 5) where at least part of the passageway 60 is open to the entryway 24 or frame 28, a person can access the room 74 by walking through the passageway 60. When the rotating entrance assembly 20 is rotated to the fully closed position (as shown in FIG. 6), the entryway 24 or frame 28 is fully blocked by the first or second shielding components 40, 50, and the room 74 can no longer be accessed. For safety reasons, the rotating entrance assembly 20 should not move when a person or object is in the passageway 60. To prevent the rotating entrance assembly 20 from being activated when a person or object is in the passageway 60, a sensor may be arranged on at least one of the first shielding component 40, second shielding component 50, or the rotating base 30 to detect whether an object is in the passageway 60. A sensor may also be placed in the floor or in the area adjacent to the rotating entrance assembly 20 to detect when a person or object is approaching the passageway 60. Preferably, a plurality of sensors are used to enhance accuracy. The sensor may be, for example and without limitation, a pressure sensor arranged in the rotating base 30 or a motion sensor arranged in the first and second shielding components 40, 50. The sensor may be configured to relay signals to a control system electrically connected to the motor to control operation of the rotating entrance assembly 20. When the sensor detects a person or object in the passageway 60, the control system prevents the motor 36 from moving the rotating entrance assembly 20.

In order to further prevent an object such as a person's limb or clothing from getting caught between the passageway 60 and wall 26 as the rotating entrance assembly 20 moves between the open and closed positions, each one of the opposing openings 62 of the passageway 60 may be equipped with a movable barrier element 64, as shown by the dotted line in FIG. 2. The movable barrier element 64 may be, for example and without limitation, a clear acrylic curved door panel mounted between the first and second shielding components 40, 50. The movable barrier element 64 is opened when the rotating entrance assembly 20 is in the fully opened position (FIG. 4) or diagnostic open position (FIG. 5) to allow a person to access the room, and closed when the rotating entrance assembly 20 is rotated between the fully opened position or diagnostic open position and the fully closed position (FIG. 6) so that nothing can be caught in the passageway 60. Alternatively, the movable barrier element 64 can be mounted on the entryway 24 or frame 28 and selectively opened and closed to access the rotating entrance assembly 20.

Figure 9:
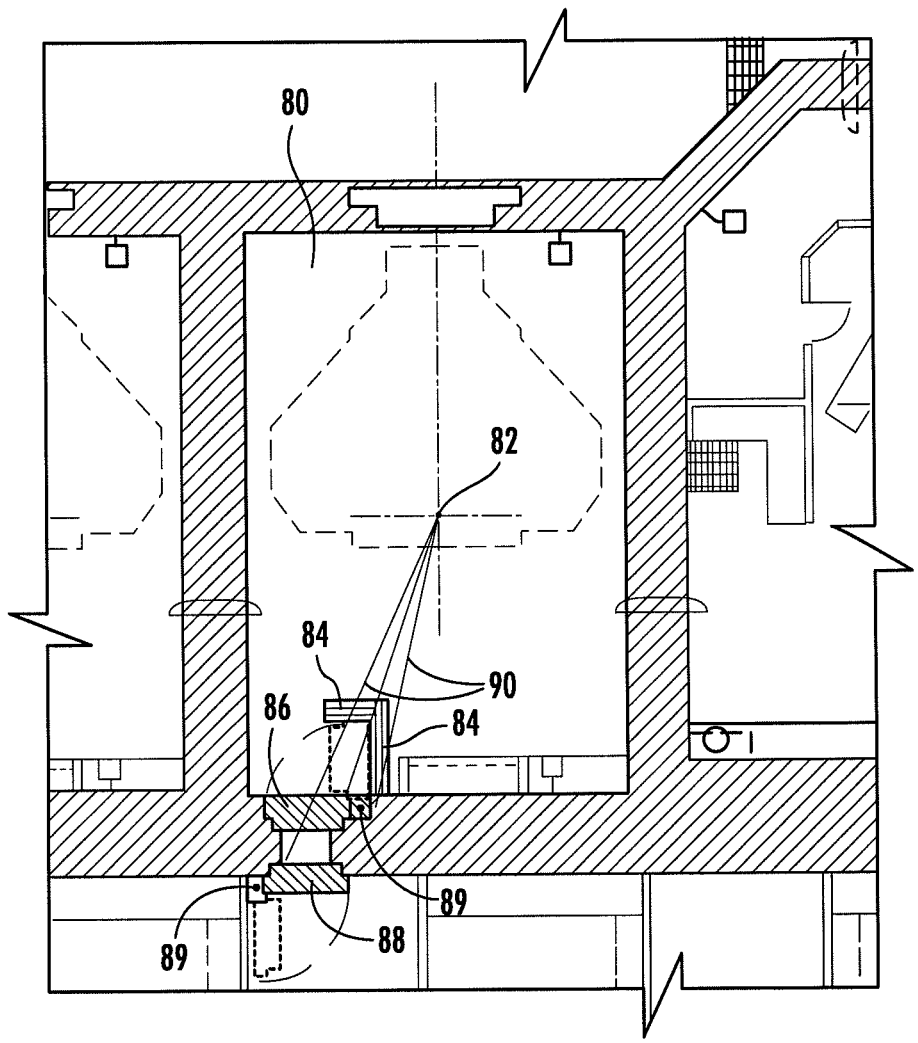
FIG. 9 is a top view of a conventional particle facility room equipped with a mini maze entry and double shielded doors.

The rotating entrance assembly 20 according to the present application is especially advantageous when used in particle facilities such as medical treatment rooms, where multiple rounds of low energy radiation are used for diagnostics or testing, between which rounds an operator must enter and exit the treatment room to adjust the patient or equipment. FIG. 9 shows a radiation room 80 housing a radiation source 82 and having a mini maze entry, which uses a wing wall 84 to capture scatter radiation 90 from the radiation source 82. The entrance to the radiation room 80 shown in FIG. 9 also includes inner and outer shielded doors 86, 88 to further prevent radiation leakage to the outside of the room 80. The inner and outer shielded doors 86, 88 are each constructed as a hinged door that rotates about a hinge 89 located in a sidewall of the room 80. As shown by FIG. 9, in certain applications the wing wall 84 and inner shielded door 86 alone may be insufficient to capture all of the scatter radiation 90, thus requiring the outer shielded door 88. The inner and outer shielded doors 86, 88 may be synchronized to open and close at the same time, or individually opened and closed, further increasing the time it takes to access the room 80. When low energy radiation is used for diagnostic or testing purposes, the operator must enter the room 80 after each round of low energy radiation to make adjustments to the patient or equipment. This process can be very time consuming, as the inner and outer shielded doors 86, 88 must be fully closed during each round of low energy radiation, then fully opened to allow the operator to access the room 80, taking at least 10-12 seconds each time.

Figure 7:
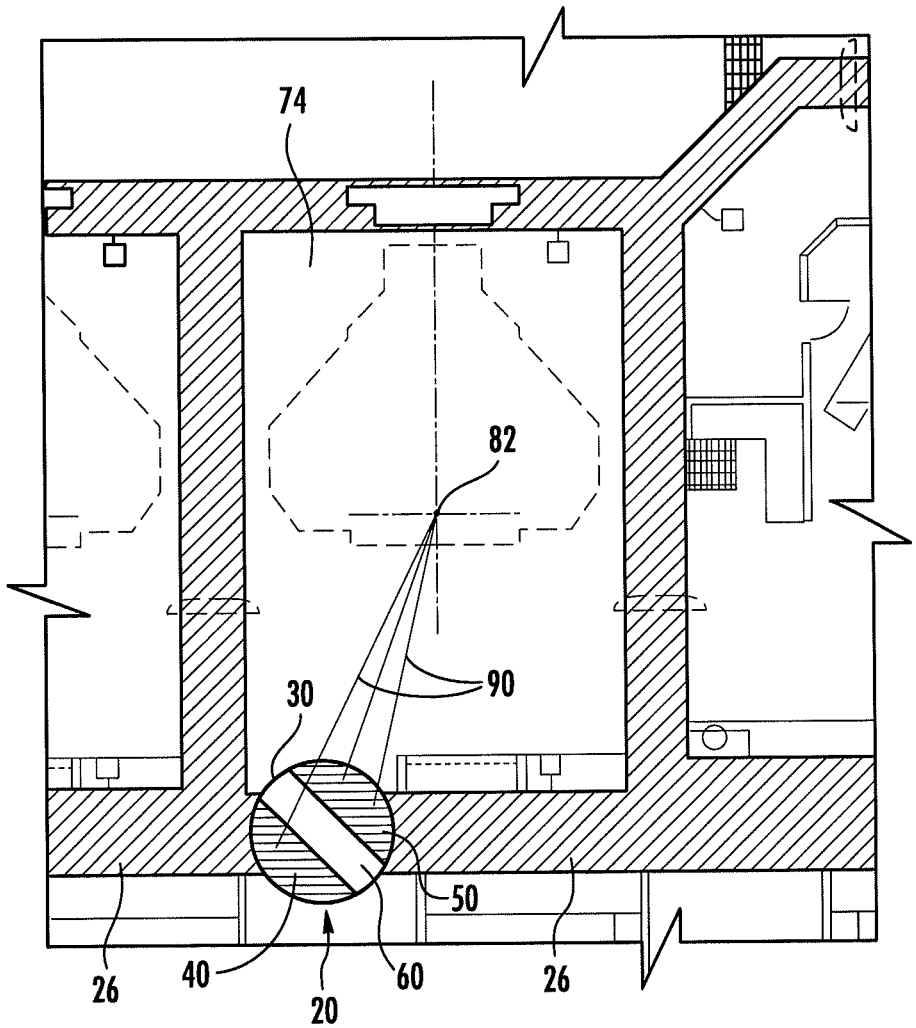
FIG. 7 is an enlarged detail view of the area circled in FIG. 5.
Figure 8:
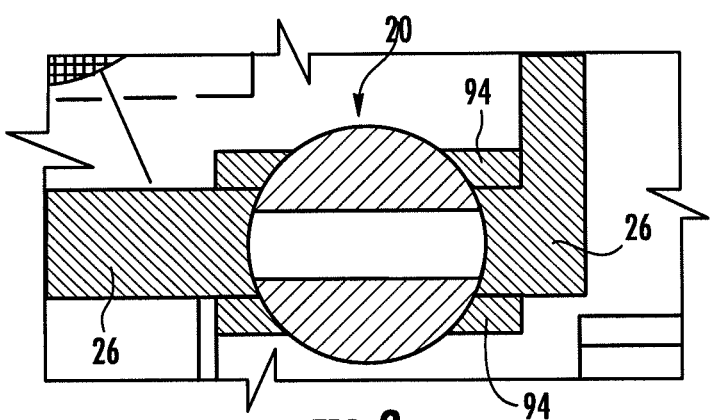
FIG. 8 is an enlarged detail view of the area circled in FIG. 6.

The rotating entrance assembly 20 according to the present application provides a solution to this problem, as the rotating entrance assembly 20 can be kept at a "diagnostic open position" during the rounds of low energy radiation testing. The diagnostic open position refers to a position in which the passageway 60 is arranged at an oblique angle with respect to the wall 26 of the room and is still open to the entryway 24 or frame 28, as shown in FIGS. 1-3 and 5. The rotating entrance assembly 20 can be kept in the diagnostic open position during the low energy radiation testing process, without the need to be fully opened and closed like the hinged doors shown in FIG. 9. As shown in FIG. 7, when low energy radiation of approximately 90 KeV is used, scatter radiation 90 from the radiation source 82 is captured by the first and second shielding components 40, 50, which are arranged at an oblique angle with respect to the walls 26 of the room 74. After each round of low energy radiation, the operator can enter and exit the room 74 through the passageway 60, without having to wait for the rotating entrance assembly 20 to move between the fully open and fully closed positions. After the necessary adjustment have been made and high energy radiation of approximately 230 MeV in the case of a proton beam, or up to 20 MeV in the case of conventional radiotherapy photon treatments, is used, the rotating entrance assembly 20 can be quickly rotated to the fully closed position. Keeping the rotating entrance assembly 20 in the diagnostic open position during the rounds of low energy radiation testing significantly decreases the time it takes to complete the process and the opportunity for user error, as the rotating entrance assembly 20 does not need to be repeatedly opened and closed like traditional hinged shielded doors. Furthermore, as shown by FIG. 8, additional shielding can be provided by adding an additional shielding element 94 on the inside, outside, or both sides of the wall 26 at the location of the rotating entrance assembly 20. These additional shielding elements 94 add edge protection to the sides of the rotating entrance assembly 20, where the shielding material of first and second shielding components 40, 50 may not be as thick.

Highly efficient hinged shielded doors used in particle facilities take approximately 10-12 seconds to move from a fully open position to a fully closed position, and vice versa. The rotating entrance assembly 20 of the present application can move between the diagnostic open position and the fully closed position in approximately 5-6 seconds, which reduces the waiting time for a treatment technician to move in and out of the room.

As shown in FIGS. 4-6, each room 74 of a particle facility 70 that houses a radiation source 82 can be equipped with a rotating entrance assembly 20 according to the present application. Depending on the needs of the facility, the rotating entrance assemblies 20 of the rooms 74 may be synchronized or controlled individually. As shown in FIG. 5, the rotating entrance assembly 20 of one of the rooms 74 may be in the fully closed position while the rotating entrance assemblies 20 of the remaining rooms 74 are in the diagnostic open position. While the rotating entrance assembly 20 shown in FIGS. 1-3 is wider than the wall 26 and thus protrudes into the room, the size of the rotating entrance assembly 20 can be easily adjusted to match the thickness of the wall 26. The rotating entrance assembly 20 can be built as part of a new particle facility, or used in an entryway of an existing particle facility, without incurring significant construction costs. Unlike a traditional shielded door, which rotate about a hinge built into a sidewall or between the ceiling and floor of a room, the present rotating entrance assembly 20 can be easily mounted in an existing entryway without the need to build components into the wall or ceiling, which are often constructed from thick continuously poured concrete. In addition to reduced construction costs, a particle facility equipped with the present rotating entrance assembly 20 can have other cost savings that result from increased patient throughput due to the faster operating times of the rotating entrance assembly 20. The cost of constructing a proton facility is very high, and can average $200 million in investment for the required equipment and buildings. Therefore, high patent throughput is vital to the profitability of such facilities. A typical proton facility only treats approximately three (3) patients per hour. Simply increasing the patient throughput by one (1) patient per hour can make a significant financial difference.

While various methods, configurations, and features of the present invention have been described above and shown in the drawings, one of ordinary skill in the art will appreciate from this disclosure that any combination of the above features can be used without departing from the scope of the present invention. It is also recognized by those skilled in the art that changes may be made to the above described methods and embodiments without departing from the broad inventive concept thereof.

What is claimed is:

1. A rotating entrance assembly for a radiation treatment comprising:
    a rotating base that rotates about a vertical axis;
    first and second shielding components arranged on the rotating base, the first and second shielding components have spaced apart opposing planar surfaces that define a linear through passageway extending between the first and second shielding components and through the vertical axis, each of the opposing planar surfaces extending along the entire length of the linear through passageway; and a motor in driving connection with the rotating base.

2. The rotating entrance assembly of claim 1, wherein the motor is positioned below the rotating base.

3. The rotating entrance assembly of claim 2, wherein the motor is accessible through a removable panel formed in the rotating base.

4. The rotating entrance assembly of claim 1, wherein the first and second shielding components are supported by the rotating base such that the rotating base is balanced.

5. The rotating entrance assembly of claim 1, wherein the first and second shielding components are each formed of a material adapted to reflect, attenuate, or capture particles.

6. The rotating entrance assembly of claim 1, further comprising a sensor arranged on at least one of the first shielding component, the second shielding component, or the rotating base, the sensor configured to detect whether an object is in the passageway.

7. The rotating entrance assembly of claim 6, wherein the sensor is a pressure sensor.

8. The rotating entrance assembly of claim 6, wherein the sensor is a motion sensor.

9. The rotating entrance assembly of claim 6, wherein the sensor is configured to relay signals to a control system electrically connected to the motor to control operation of the rotating entrance assembly.

10. The rotating entrance assembly of claim 1, wherein each one of the first and second shielding components includes an inner surface that faces towards the passageway and a curved outer surface that faces away from the passageway.

11. The rotating entrance assembly of claim 1, wherein the rotating base is substantially circular and the vertical axis is located substantially at a center of the rotating base.

12. The rotating entrance assembly of claim 1, wherein the passageway includes opposing openings, each one of the openings of the passageway having a movable barrier element.

13. A rotating entrance assembly for a particle facility comprising:
    a frame;
    a motor driven rotating base positioned in the frame and rotatable about a vertical axis; and
    a first shielding component and a second shielding component separate from the first shielding component, the first and second shielding components are supported on the rotating base and have opposing planar walls to define a linear passageway extending between the first and second shielding components and through the vertical axis, each of the opposing planar walls extending along the entire length of the linear passageway;
    wherein the first and second shielding components and the rotating base rotate together with respect to the frame.

14. The rotating entrance assembly of claim 13, wherein the vertical axis is located substantially at a center of the rotating base.

15. The rotating entrance assembly of claim 13, wherein the first and second shielding components and the rotating base rotate between a fully open position, in which the passageway is substantially parallel to the frame, and a fully closed position, in which the passageway is substantially perpendicular to the frame.

16. The rotating entrance assembly of claim 13, wherein the first and second shielding components each has a curved outer contour that corresponds to a curved inner contour of the frame.

17. The rotating entrance assembly of claim 13, wherein the passageway has a width suitable for a person to walk through.

18. A hinge-less entrance assembly for installation in an existing entryway of a radiation treatment facility, the hinge-less entrance assembly comprising:
    a base that rotates about a vertical axis located substantially at a center of the base;
    a motor that drives the base;
    a first shielding component and a separate second shielding component arranged at a distance apart on opposing sides of the base, the first and second shielding components have spaced apart opposing planar surfaces; and
    a linear passageway defined between the first and second shielding components and through the vertical axis, each of the opposing planar surfaces extending along the entire length of the linear through passageway.

19. The hinge-less entrance assembly of claim 18, wherein a center of the base is located within the passageway.

20. The hinge-less entrance assembly of claim 18, wherein each one of the first and second shielding components has a substantially D-shaped cross-section.

21. The rotating entrance assembly of claim 1, wherein the linear passageway extends along an entire diameter of the rotating base.

* * * * *